(12) United States Patent
Porro

(10) Patent No.: US 11,976,027 B2
(45) Date of Patent: May 7, 2024

(54) HIGH PRESSURE STRIPPERS FOR USE IN UREA PLANTS

(71) Applicant: YARA INTERNATIONAL ASA, Oslo (NO)

(72) Inventor: Lino Giovanni Porro, Etterbeek (BE)

(73) Assignee: YARA INTERNATIONAL ASA, Oslo (NO)

( * ) Notice: Subject to any disclaimer, the term of this patent is extended or adjusted under 35 U.S.C. 154(b) by 390 days.

(21) Appl. No.: 17/418,512

(22) PCT Filed: Apr. 30, 2020

(86) PCT No.: PCT/EP2020/062034
§ 371 (c)(1),
(2) Date: Jun. 25, 2021

(87) PCT Pub. No.: WO2020/225093
PCT Pub. Date: Nov. 12, 2020

(65) Prior Publication Data
US 2022/0064109 A1  Mar. 3, 2022

(30) Foreign Application Priority Data
May 3, 2019  (EP) ..................... 19172462

(51) Int. Cl.
| | | |
|---|---|---|
| *C07C 273/16* | (2006.01) | |
| *B01J 8/06* | (2006.01) | |
| *B01J 19/00* | (2006.01) | |
| *B01J 19/24* | (2006.01) | |
| *C07C 269/08* | (2006.01) | |

(52) U.S. Cl.
CPC ............ *C07C 273/16* (2013.01); *B01J 8/067* (2013.01); *B01J 19/0013* (2013.01);
(Continued)

(58) Field of Classification Search
CPC ..... C07C 273/16; C07C 273/04; B01D 5/006; B01D 5/0075; B01J 19/006;
(Continued)

(56) References Cited

U.S. PATENT DOCUMENTS

| | | |
|---|---|---|
| 5,653,282 A | 8/1997 | Hackemesser |
| 7,842,255 B2 | 11/2010 | Pennino |

(Continued)

FOREIGN PATENT DOCUMENTS

| | | |
|---|---|---|
| CN | 106237936 A | 12/2016 |
| EP | 0002298 A2 | 6/1979 |

(Continued)

OTHER PUBLICATIONS

Indian Office Action issued in App. No. IN202117052380, dated May 3, 2023, 6 pages.

(Continued)

*Primary Examiner* — Renee Robinson
(74) *Attorney, Agent, or Firm* — Dilworth IP, LLC

(57) ABSTRACT

Shell-and-tube strippers for stripping a urea/carbamate mixture, related systems, methods, and uses. The stripper includes a shell, a plurality of tubes disposed within the shell, and a heating fluid distributor for homogenizing the flow of a heating fluid near a heating fluid inlet. The heating fluid distributor includes an edge wall and a laterally disposed heating fluid distribution plate. Related systems, methods, and uses are also provided.

20 Claims, 9 Drawing Sheets

(52) U.S. Cl.
CPC ......... *B01J 19/006* (2013.01); *B01J 19/2425* (2013.01); *C07C 269/08* (2013.01); *B01J 2208/00849* (2013.01); *B01J 2208/00938* (2013.01); *B01J 2208/065* (2013.01); *B01J 2219/00081* (2013.01); *B01J 2219/00099* (2013.01); *B01J 2219/185* (2013.01); *B01J 2219/1943* (2013.01)

(58) Field of Classification Search
CPC ... B01J 2219/00081; B01J 2208/00938; F28D 7/00; F28F 9/22; F28F 19/00; F28F 19/002
See application file for complete search history.

(56) References Cited

U.S. PATENT DOCUMENTS

| | | | |
|---|---|---|---|
| 8,168,131 | B2 | 5/2012 | Burlingame |
| 2001/0031839 | A1 | 10/2001 | Muller |

FOREIGN PATENT DOCUMENTS

| | | |
|---|---|---|
| EP | 0002298 B1 | 1/1981 |
| RU | 2233836 C2 | 8/2004 |
| RU | 2502031 C2 | 12/2013 |
| WO | 2010006757 A1 | 1/2010 |
| WO | 2018/019760 A1 | 2/2018 |
| WO | 2019/081686 A1 | 5/2019 |

OTHER PUBLICATIONS

European Search Report in related EP Application No. 19172462.4; dated Oct. 2, 2019; 6 pages.
International Search Report and Written Opinion in related PCT/EP2020/062034; dated Oct. 28, 2020; 14 pages.
Russian Office Action issued in App. No. RU2021135475/04, dated Sep. 29, 2023, 16 pages.

HIGH PRESSURE STRIPPERS FOR USE IN UREA PLANTS

TECHNICAL FIELD

The present invention is in the field of urea manufacture, in particular in the field of high pressure strippers for decomposing carbamate and stripping ammonia in urea/carbamate mixtures from urea reactors in urea plants.

BACKGROUND

High Pressure Strippers are used in urea plants to concentrate urea, by removing the carbamate from a liquid urea/carbamate mixture. The urea/carbamate mixture is a solution of urea, ammonium carbamate, free ammonia and water, coming from a reactor in which urea is formed by the reaction of ammonia and $CO_2$ into ammonium carbamate (also referred to as carbamate) and subsequent dehydration of carbamate to produce urea. The conversion of carbamate into urea is, in practical terms, never complete and the solution leaving the urea reactor always comprises some carbamate and free ammonia.

A common way of removing carbamate and of concentrating the solution involves the use of a tube heat exchanger, called High Pressure Stripper, operating at a similar pressure to that of the urea reactor. Under the influence of the heat provided by a heating medium such as steam, the ammonium carbamate in the urea and carbamate mixture decomposes to form gaseous $NH_3$ and $CO_2$. These $NH_3$ and $CO_2$ gases are removed from the stripper. Accordingly, urea/carbamate solution concentrated in urea is produced which is collected at the bottom of the stripper.

Two categories of high-pressure strippers currently exist: $CO_2$ strippers and self-strippers. In $CO_2$ strippers, $CO_2$ is used as a stripping gas. It is fed to the bottom of the High Pressure Stripper and $NH_3$ and $CO_2$ produced during the decomposition of ammonium carbamate are entrained by the $CO_2$ stripping gas.

In self-strippers, no stripping gas is added to the stripper, but $NH_3$ and $CO_2$ formed during the decomposition of ammonium carbamate serve as the stripping gas.

The strippers comprise tubes and a shell, a top end, and a bottom end. During normal use, the top end is situated at the top of the stripper and the bottom end is situated at the bottom of the stripper. At the top end, a urea/carbamate mixture is distributed in the tubes and a gas mixture comprising stripping gas and entrained $NH_3$ and $CO_2$ formed during carbamate decomposition leave the stripper. At the bottom end, the stripped urea solution is collected. In the case of $CO_2$ strippers, $CO_2$ stripping gas is provided to the bottom end of stripper.

During normal operation, the tubes are installed substantially vertically. They enclose a tube-side space. A shell-side space is disposed between the tubes and the shell. The stripping gas and the urea/carbamate mixture run counter-current through the tube-side space while the urea/carbamate mixture is heated by means of a heating medium in the shell-side space, commonly steam. The urea/carbamate mixture flows into the tubes in a falling film pattern, while the gases rise in the inner part of the tubes. U.S. Pat. No. 5,653,282 discloses a shell-and-tube heat exchanger with impingement distributor, wherein the impingement distributor has a cylindrical distribution plate with evenly arranged rows of longitudinal perforations and a plurality of impact bars longitudinally aligned with the perforations. This way, the hot fluid impinges on the impact bars and direct impingement on the tubes is avoided.

EP0002298 discloses a process and apparatus for the removal of ammonium carbamate from a urea-synthesis solution, wherein an aqueous urea solution is introduced into a stripping zone and caused to flow down a heat-exchange wall as a thin film while being heated and contacted in counter-current relation with a gaseous stripping agent.

It would be desirable to scale up such strippers in order to manufacture large volumes of urea in a cost-efficient way. Unfortunately, scaling up these strippers is not always easy and many unforeseen problems tend to occur during upscaling.

SUMMARY

The inventors identified two issues during upscaling of shell-and-tube strippers: severe tube corrosion and inefficient stripping. These issues are solved by way of the presently disclosed strippers, systems, and methods.

In particular, provided herein is a shell-and-tube stripper for stripping a urea/carbamate mixture, the stripper comprising a top end in fluid connection with a bottom end through a plurality of tubes disposed within a shell; the top end comprising an inlet for a urea/carbamate mixture and an outlet for a gas mixture comprising the stripping gas and one or more stripped compounds; the bottom end comprising an outlet for a urea/carbamate stream concentrated in urea; the bottom end optionally comprising an inlet for a stripping gas; the shell-and-tube stripper further comprising a heating fluid inlet and a heating fluid outlet in fluid connection with a shell-side space disposed between the plurality of tubes and the shell; the shell-and-tube stripper having a longitudinal direction and lateral cross sections, the longitudinal direction being parallel to the tubes and the lateral cross sections being perpendicular to the longitudinal direction; wherein the shell-and-tube stripper comprises a heating fluid distributor near the heating fluid inlet for homogenizing the flow of heating fluid in the stripper, the heating fluid distributor comprising an edge wall and a heating fluid distribution plate which is disposed parallel to the lateral cross sections; the edge wall comprising two or more openings and/or a plurality of perforations, and the edge wall defining a belt-shaped space between the shell and the edge wall; the heating fluid inlet being arranged for providing heating fluid to the belt-shaped space; the belt-shaped space being arranged for providing heating fluid to an inner heating fluid distribution space; the heating fluid distribution plate being arranged for providing heating fluid from the inner heating fluid distribution space to the shell-side space between the heating fluid distributor and the bottom end; the heating fluid distribution plate comprising a plurality of perforations, the plurality of perforations comprising a plurality of tube holes and a plurality of heating fluid holes, wherein the size and/or the density of the heating fluid holes changes in the radial direction of the heating fluid distribution plate.

In some embodiments, the size of the heating fluid holes changes from the centre of the heating fluid distribution plate towards the outer rim of the heating fluid distribution plate.

In some embodiments, means for limiting vibrations of the tubes are provided between the heating fluid distribution plate and the bottom end, optionally wherein the means for limiting vibrations of the tubes comprise a plurality of rod baffles.

In some embodiments, the angle between the longitudinal direction and the heating fluid distribution plate is from 85.0° to 90.0°, or from 87.5 to 90.0°, or from 88.0° to 90.0°, preferably from 89.0° to 90.0°, more preferably from 89.5° to 90.0°, even more preferably 90.0°; and/or wherein the angle between the longitudinal direction and the edge wall is from 0.0° to 5.0°, or from 0.0° to 2.5°, or from 0.0° to 2.0°, preferably from 0.0° to 1.0°, more preferably from 0.0° to 0.5°, even more preferably 0.0°.

In some embodiments, the size of the heating fluid holes increases from the outer rim to the centre of the heating fluid distribution plate, optionally wherein the size of the heating fluid holes strictly increases from the outer rim to the centre of the heating fluid distribution plate; or wherein the size of the heating fluid holes decreases from the outer rim to the centre of the heating fluid distribution plate, optionally wherein the size of the heating fluid holes strictly decreases from the outer rim to the centre of the heating fluid distribution plate.

In some embodiments, the heating fluid distribution plate comprises one or more areas in which the size of the heating fluid holes strictly decreases from the outer rim to the centre of the heating fluid distribution plate, and wherein the heating fluid distribution plate comprises one or more areas in which the size of the heating fluid holes strictly increases from the outer rim to the centre of the heating fluid distribution plate.

In some embodiments, the diameter of the heating fluid holes is from at least 1 mm to at most 16 mm, preferably from at least 2 mm to at most 13 mm, more preferably from at least 3 mm to at most 10 mm, even more preferably from at least 5 mm to at most 7 mm.

In some embodiments, the ratio of the diameter of the largest heating fluid holes on the one hand, and the diameter of the smallest heating fluid holes on the other hand is from at least 1.1 to at most 16, preferably from at least 1.4 to at most 3.5.

In some embodiments, the heating fluid holes in the heating fluid distribution plate are evenly spaced at concentric circles around the centre of the heating fluid distribution plate.

In some embodiments, the density of heating fluid holes is constant in the heating fluid distribution plate, wherein the size of the heating fluid holes changes from the centre of the heating fluid distribution plate towards the outer rim of the heating fluid distribution plate, wherein the tube holes are arranged in a triangular geometry, and wherein each heating fluid hole is centrally disposed between three adjacent tube holes.

In some embodiments, the density of heating fluid holes is constant in the heating fluid distribution plate the size of the heating fluid holes changes from the centre of the heating fluid distribution plate towards the outer rim of the heating fluid distribution plate, the tube holes are arranged in a square geometry, wherein each heating fluid hole is centrally disposed between four adjacent tube holes.

In some embodiments, the stripper comprises more than 3000 tubes, or more than 4000 tubes, or more than 5000 tubes, or more than 6000 tubes, or more than 7000 tubes, or 3000 to 7000 tubes, or 4000 to 6000 tubes, or 5000 to 7000 tubes, or 5000 to 10000 tubes.

Further provided is a system for the production of urea comprising a carbamate condenser, a urea reactor, and a shell-and-tube stripper as described herein.

Further provided is the use of a shell-and tube stripper according as described herein for stripping a urea-carbamate mixture.

Further provided is a method for stripping a urea/carbamate mixture, the method comprising the steps: providing a shell-and-tube stripper as described herein; providing the urea/carbamate mixture to the inlet for the urea/carbamate mixture; providing a heating fluid to the shell-side space by means of the heating fluid inlet, wherein the heating fluid is saturated steam; optionally providing a stripping gas to the inlet for a stripping gas at the bottom end; contacting the urea/carbamate mixture and the stripping gas in a tube-side space disposed within the tubes, and heating the urea/carbamate mixture by means of the heating fluid, thereby obtaining a urea/carbamate stream concentrated in urea; extracting the urea/carbamate stream concentrated in urea at the outlet for the urea/carbamate stream concentrated in urea; extracting a gas mixture comprising one or more stripped compounds at the outlet for the gas mixture, the one or more stripped compounds comprising $NH_3$, $CO_2$, and water; extracting the heating fluid at the heating fluid outlet.

Further provided is the use of a heating fluid distributor for homogenizing the flow of steam near a heating fluid inlet of a shell-and-tube stripper for stripping a urea/carbamate mixture, the heating fluid distributor comprising an edge wall and a heating fluid distribution plate which is disposed parallel to the lateral cross sections; the edge wall comprising two or more openings and/or a plurality of perforations, the heating fluid distribution plate having a an outer rim and a centre, the heating fluid distribution plate comprising a plurality of perforations, the plurality of perforations comprising a plurality of tube holes and a plurality of heating fluid holes, wherein the size and/or the density of the heating fluid holes changes from the centre of the heating fluid distribution plate towards the outer rim of the heating fluid distribution plate.

DESCRIPTION OF THE FIGURES

The following description of the figures of specific embodiments of the invention is only given by way of example and is not intended to limit the present explanation, its application or use. In the drawings, identical reference numerals refer to the same or similar parts and features.

Figure 1:
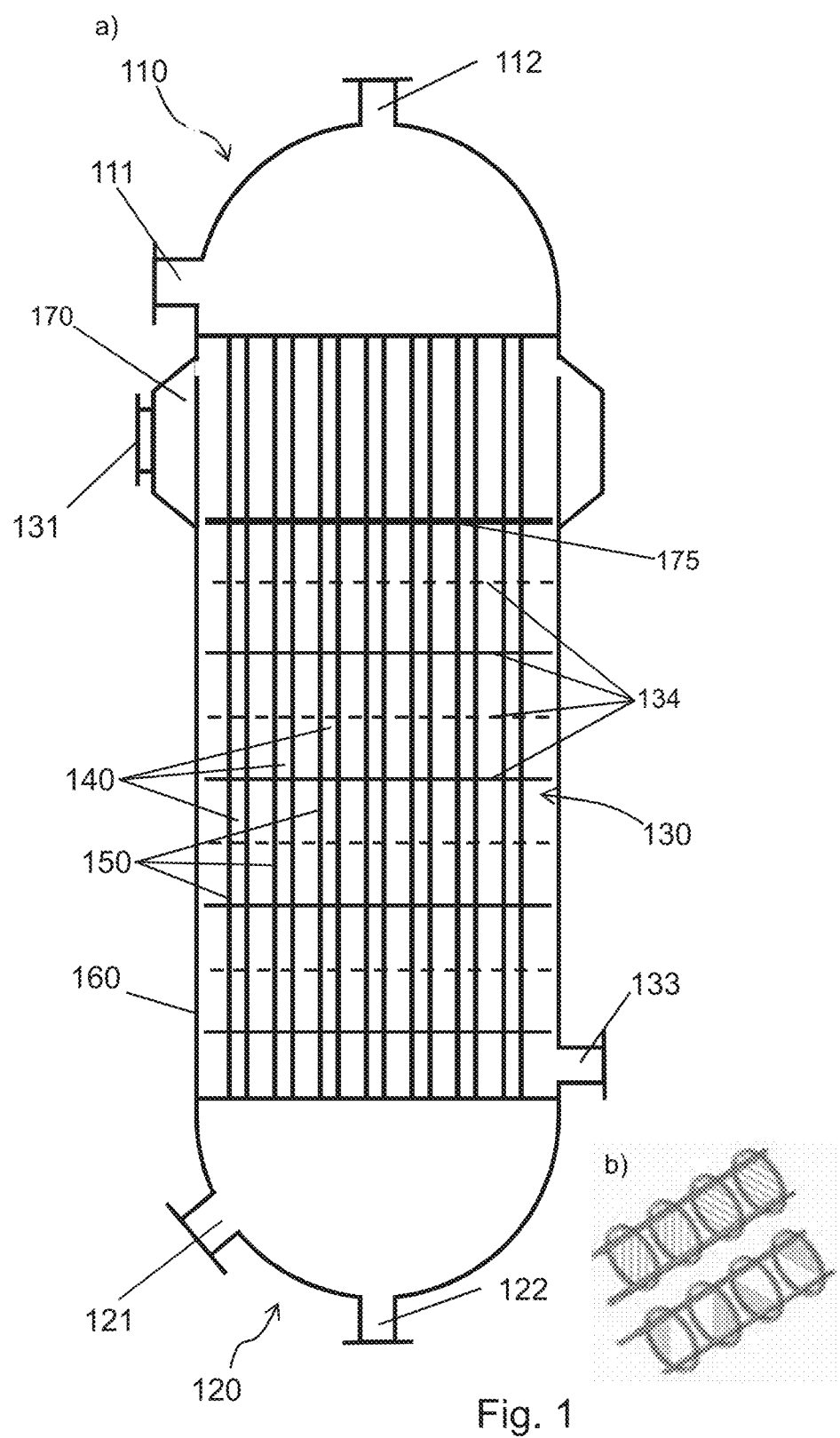
FIG. 1 shows an embodiment of a $CO_2$ stripper (100).

The following reference numerals are used in the description and figures:

100 stripper; 101—stripping gas feed; 102—tube for a urea/carbamate stream; 103—tube for stream comprising stripping gas and one or more stripped compounds; 104—tube for a urea/carbamate stream concentrated in urea; 110—top end (on top of the stripper during normal use); 111—inlet for a urea/carbamate mixture; 112—outlet for a gas mixture; 120—bottom end (at the bottom of the stripper during normal use); 121—inlet for stripping gas; 122—outlet for a urea/carbamate solution concentrated in urea; 130—shell-side space; 131—heating fluid inlet; 133—heating fluid outlet; 134—rod baffles; 140—tube-side space; 150—tube; 151—top tube sheet; 152—bottom tube sheet; 153—corrosion area; 154—scaling area; 155—stream lines (lateral steam flow); 156—stream lines (longitudinal steam flow); 157—stream lines (flow in heating fluid distributor) 160—shell; 170—heating fluid distributor; 171—edge wall; 172—thermal expansion space; 174—edge wall opening; 175—heating fluid distribution plate; 176—tube hole; 177—steam hole; 178—inner heating fluid distribution space; 179—belt-shaped space; 200—reactor; 201—tube for vapours of $NH_3$, $CO_2$, water, and inerts; 300—carbamate condenser; 301—tube for gaseous stream; 302—tube for carbamate solution stream; 400—scrubber; 401—tube for carbamate solution feed from downstream section; 402—tube for stream of inert gases; 500—heating fluid supply; 501—vapour generator; 502—connection to external heating fluid supply; 503—tube for heating fluid stream; 504—tube for cooled heating fluid stream; 600—high-pressure injector; 601—ammonia feed; 700—ferrule; 710—hole for urea/carbamate mixture; 720—hole for gas; 800—obstructed area; 810—unobstructed area; 1000—high pressure section of a urea plant.

DESCRIPTION OF THE INVENTION

As used below in this text, the singular forms "a", "an", "the" include both the singular and the plural, unless the context clearly indicates otherwise.

The terms "comprise", "comprises" as used below are synonymous with "including", "include" or "contain", "contains" and are inclusive or open and do not exclude additional unmentioned parts, elements or method steps. Where this description refers to a product or process which "comprises" specific features, parts or steps, this refers to the possibility that other features, parts or steps may also be present, but may also refer to embodiments which only contain the listed features, parts or steps.

The enumeration of numeric values by means of ranges of figures comprises all values and fractions in these ranges, as well as the cited end points.

All references cited in this description are hereby deemed to be incorporated in their entirety by way of reference.

Unless defined otherwise, all terms disclosed in the invention, including technical and scientific terms, have the meaning which a person skilled in the art usually gives them. For further guidance, definitions are included to further explain terms which are used in the description of the invention.

In the process of scaling up high-pressure shell-and-tube strippers for decomposition of urea-carbamate mixtures a remarkable corrosion pattern was observed. In particular, it was found that some tubes in high-pressure strippers for decomposition of urea-carbamate mixtures suffer from more severe corrosion compared to others. Without the invention being bound by any particular theory or mode of operation, it is believed that the corrosion-related issues are related to tube corrosion induced by ammonium carbamate at high temperature. It was further discovered that the corrosion-related issues can be explained by inhomogeneous heating of the tubes; ammonium carbamate causes more severe corrosion at higher temperatures such that inhomogeneous heating of the tubes causes inhomogeneous corrosion. During normal operation, the methods and devices disclosed herein improve temperature homogeneity in the liquid ammonium carbamate phase and as a consequence, lateral temperature variations are reduced. This in turn improves the homogeneity by which the tubes are heated, reduces tube corrosion, and increases the useful life of strippers.

The inventors further discovered that the corrosion-related issues can be solved by means of the stripper designs disclosed herein. Thus, it can be ensured that the tubes in the strippers according to the present invention have an expected lifetime of around 20 to 30 years.

While the present invention was discovered in the context of scaling up strippers, it is not believed that the advantages offered by the present invention are anyhow limited to strippers of any particular size.

The term "carbamate" as used herein refers to ammonium carbamate. The term "urea/carbamate mixture" as used herein refers to a mixture comprising urea, ammonium carbamate, ammonia, and water. In some embodiments, the urea/carbamate mixture consists of 31 to 34 wt % urea, 32 to 35 wt % ammonium carbamate, 16 to 18 wt % ammonia, 0.1 to 0.3 wt % biuret, the balance being made up of water. The symbol wt % here refers to the weight percentage of the constituents with respect to the urea/carbamate mixture.

The expression "stripping a urea/carbamate mixture" as used herein refers to a process of decomposing ammonium carbamate comprised in the mixture to form ammonia and carbon dioxide. The formed ammonia and carbon dioxide are entrained by a stripping gas. Also, water comprised in the urea/carbamate mixture is at least partially entrained by the stripping gas as well.

The terms "upstream" and "downstream" as used herein have the following meaning: upstream is the direction towards the heating fluid inlet. Downstream is the direction towards the heating fluid outlet.

The term "vertical" as used herein is explained as follows: when objects are said to be vertically oriented, reference is made to the orientation of their longitudinal axis. It shall be understood that this orientation may have a certain deviation from the vertical axis.

Preferably, this deviation is less than 1.0°, or less than 0.5°. More preferably, the deviation is less than 0.1°.

The expression "near the heating fluid inlet" as used herein, when used to describe the position of the heating fluid distributor, indicates that the heating fluid distributor is at the same, or at substantially the same, longitudinal position in the stripper.

The stripper is particularly useful as a high-pressure stripper in a urea plant that also contains a urea reactor. Such strippers commonly operate at a pressure which is similar to that of the urea reactor, e.g. equal to within a margin of 5.0%.

Provided herein is a stripper, in particular a shell-and-tube stripper, for stripping a urea/carbamate mixture. The present invention is applicable to any kind of stripper for stripping urea/carbamate mixtures. In particular, it is applicable to both self-strippers and $CO_2$ strippers. In $CO_2$ strippers, $CO_2$ is used as a stripping gas. It is fed to the bottom of the High Pressure Stripper and $NH_3$ and $CO_2$ produced during the decomposition of ammonium carbamate are entrained by the $CO_2$ stripping gas. In self-strippers, no stripping gas is added to the stripper, but $NH_3$ and $CO_2$ formed during the decomposition of ammonium carbamate serve as the stripping gas.

Accordingly, in some embodiments, the stripper is a $CO_2$ stripper, and the stripping gas is $CO_2$.

Alternatively, in some embodiments, the stripper is a self-stripper, and the stripping gas is $NH_3$ and $CO_2$ generated by decomposition of the carbamate. When the stripper is a self-stripper, its bottom end does not comprise an inlet for a stripping gas. This notwithstanding, the bottom-end of self-strippers preferably does comprise an inlet for a passivating gas stream. Preferably, air is used as a passivating gas stream. Note thought that the flow rates of the passivating air stream are so low that they do not contribute in any meaningful way to the stripping process itself. Typical flow rates of passivating air are 50 to 250 kg/hour, or 50 to 500 kg/hour of air.

The stripper has a longitudinal direction and a lateral cross section. The longitudinal direction is parallel to the tubes. The lateral cross section is perpendicular to the longitudinal direction. In other words, the longitudinal direction is the direction which connects the top end and the bottom end. The lateral cross sections are perpendicular to the longitudinal direction. In other words, the term "lateral cross section through the stripper" refers to a cross section through the stripper in a plane which is perpendicular to the tubes. Preferably, the stripper is cylindrical. In other words, the stripper preferably has a circular lateral cross section.

The stripper comprises a top end and a bottom end. The top and bottom ends are in fluid connection through a plurality of tubes. The tubes are disposed within a shell. During normal use, the top end of the stripper is positioned at the top of the stripper, and the bottom end is positioned at the bottom of the stripper.

In other words, the top end is in fluid connection with the bottom end through the plurality of tubes disposed within the shell. The shell-side space is not in fluid connection with the top end and the bottom end. The shell-side space is separated from the top end, for example by means of a top tube sheet. The shell-side space is separated from the bottom end, for example by means of a bottom tube sheet. When the top end is separated from the shell-side space by means of a top tube sheet, the fluid connection between the tubes and the top end is provided by means of perforations in the top tube sheet. When the bottom end is separated from the shell-side space by means of a bottom tube sheet, the fluid connection between the tubes and the bottom end is provided by means of perforations in the bottom tube sheet. Preferably the perforations in the top tube sheet and in the bottom tube sheet are circular, the tubes are cylindrical, and the perforations have a diameter which equals the diameter of the tubes within a margin of error of less than 10.0%, 5.0%, 2.0%, or 1.0%.

The top end comprises an inlet for a urea/carbamate mixture and an outlet for a gas mixture comprising the stripping gas and one or more stripped compounds.

The bottom end comprises an outlet for a urea/carbamate stream concentrated in urea. In some embodiments, this urea/carbamate stream concentrated in urea comprises unreacted ammonium carbamate, e.g. between 0.0 and 30.0 wt %, or between 10.0 and 20.0 wt %, or between 10.0 and 15.0 wt %, or between 15.0 and 25.0 wt % of ammonium carbamate.

In some embodiments, the urea/carbamate stream concentrated in urea comprises free ammonia, e.g. between 0.0 and 20.0 wt %, or between 0.5 and 1.0 wt %, or between 0.5 and 20.0 wt %, or between 10.0 and 15.0 wt % of free ammonia.

The symbol wt % here refers to the weight percentage of the constituents with respect to the urea/carbamate stream.

In some embodiments, the urea/carbamate stream concentrated in urea comprises both free ammonia and ammonium carbamate, for example in the above-specified concentrations.

Optionally, the bottom end comprises an inlet for a stripping gas. In particular, in the case of a $CO_2$ stripper, the bottom end comprises an inlet for $CO_2$ used as a stripping gas. In the case of a self stripper, the bottom end does not comprise an inlet for a stripping gas.

The stripper further comprises a heating fluid inlet and a heating fluid outlet, both of which are in fluid connection with a shell-side space disposed between the tubes and the shell.

Preferably, the heating fluid inlet is adjacently disposed to the top end of the stripper and the heating fluid outlet is adjacently disposed to the bottom end of the stripper.

The shell-and-tube stripper comprises a heating fluid distributor near the heating fluid inlet. The heating fluid distributor allows homogenizing the flow of heating fluid in the stripper.

The heating fluid distributor comprises an edge wall and a heating fluid distribution plate which is laterally disposed in the stripper. It is understood that the expression "laterally disposed" as used herein, when referring to the heating fluid distribution plate, indicates that the heating fluid distribution plate is parallel to the lateral cross sections, or stated differently, that the heating fluid distribution plate is disposed perpendicularly to the longitudinal direction.

The edge wall comprises two or more openings and/or a plurality of perforations and the edge wall defines a belt-shaped space between the shell and the edge wall. In some embodiments, the perforations are circular. Such an edge wall reduces the speed of the steam flow as it impinges on the tubes in the stripper, thereby reducing tube erosion.

The heating fluid inlet is arranged for providing heating fluid to the belt-shaped space. Preferably, this is done by directly providing heating fluid to the belt-shaped space via the heating fluid inlet.

The belt-shaped space is arranged for providing heating fluid to an inner heating fluid distribution space. In particular, the two or more openings and/or plurality of perforations in the edge wall allow providing uniformly providing the heating fluid to the inner heating fluid distribution space.

The heating fluid distribution plate is arranged for providing heating fluid from the inner heating fluid distribution space to the shell-side space between the heating fluid distributor and the bottom end. In particular, heating fluid is provided to the shell-side space by means of a plurality of perforations comprised in the heating fluid distribution plate. The plurality of perforations comprises a plurality of tube holes and a plurality of heating fluid holes. The size and/or the density of the heating fluid holes changes in the radial direction of the heating fluid distribution plate.

The term "radial direction" as used herein refers to a direction in a lateral plane which points away from the centre of the stripper. Each radial direction corresponds to a tangential direction which is in the lateral plane and which is perpendicular to the radial direction. In some embodiments, the size of the tube hole changes in the radial directions, and is constant in the tangential directions. This results in a rotationally symmetrical arrangement of the tube hole size.

In some embodiments, the space between any tube and the tube hole through which it protrudes is less than 1.0%, 2.0%, 3.0%, 5.0%, or 10.0% of the diameter of the tube. In some embodiments, the space between any tube and the tube hole through which it protrudes the heating fluid distribution plate is between 0.0% and 1.0%, or between 1.0% and 2.0%, or between 2.0% and 3.0%, or between 3.0% and 5.0%, or between 5.0% and 10.0%, or between 0.5% and 1.5%, or between 1.5% and 2.5%, or between 2.5% and 3.5%, or between 3.5% and 5.5%, or between 5.5% and 10.5% of the diameter of the tube.

Accordingly, the shape of the perforations closely conforms to the edge of the tubes which protrude through the distribution plate. Where needed, the size margin between the tube and the edge of the perforation to allow for accommodating thermal strain in the stripper.

In some embodiments, the shell is cylindrical, and the shell has an outer diameter between 2.0 and 6.0 m, or between 3.0 and 5.0 m.

In some embodiments, the top end of the stripper is connected to the tubes by means of ferrules in a top tube sheet. Each ferrule is a liquid divider and is coupled with the tubes. The ferrules are configured to evenly distribute a urea/carbamate mixture through each tube via holes in the ferrule. Preferably, the holes are provided in the bottom part of the ferrule. Also, the ferrules comprise one or more holes, preferably in their top part, which allow releasing gas flow to the top end of the stripper.

Preferably, the edge wall of the heating fluid distributor is made out of sheet metal, for example a steel sheet.

In some embodiments, the edge wall comprises three openings in its side: a central opening and two side openings.

The openings may be, for example, rectangular or circular. For example, the heating fluid distributor comprises from 2 to 1000 openings, for example from 5 to 500 openings, or from 10 to 250 openings, or from 50 to 225 openings, or from 100 to 200 openings, or from 150 to 175 openings.

In some embodiments, the total area of the openings or perforations in the heating fluid distributor equals 2 to 8 times, or 3 to 6 times, or 4 times the total area of the corresponding heating fluid inlet.

Preferably, the height of the edge wall of the heating fluid distributor is smaller than the height of the inlet, and the height of the belt-shaped space. In other words, in these embodiments, an empty space through which a limited amount of steam can flow is left at the top of the belt-shaped space between the edge wall and the stripper's shell. An exemplary embodiment of this configuration is shown in FIG. 3b).

Preferably, the edge wall does not comprise an opening directly in front of the heating fluid inlet.

In some embodiments, the edge wall of the heating fluid distributor comprises a perforated area and a non-perforated area. In the non-perforated area, the edge wall is closed.

In some embodiments, the perforated area is adjacently disposed next to the heating fluid inlet. Consequently, the non-perforated area is positioned away from the heating fluid inlet. In some embodiments, the perforated area is positioned away from the heating fluid inlet. Consequently, the non-perforated area is positioned adjacently to the heating fluid inlet.

In some embodiments, the edge wall comprises a plurality of perforations the density and/or size of which varies over its surface. Preferably, the edge wall comprises perforations which are distributed uniformly over its surface, the size of which changes with increasing distance from the heating fluid inlet.

In some embodiments, the edge wall comprises perforations which are distributed uniformly over its surface and the size of the perforations increases, e.g. strictly increases, with increasing distance from the heating fluid inlet.

In some embodiments, the edge wall comprises perforations which are distributed uniformly over its surface and the size of the perforations decreases, e.g. strictly decreases, with increasing distance from the heating fluid inlet.

In some embodiments, the edge wall comprises perforations which are distributed uniformly over its surface and it comprises areas in which the size of the perforations increases, e.g. strictly increases, with increasing distance from the heating fluid inlet; and it comprises areas in which the size of the perforations decreases, e.g. strictly decreases, with increasing distance from the heating fluid inlet.

In some embodiments, the size of the heating fluid holes changes from the centre of the heating fluid distribution plate towards the outer rim of the heating fluid distribution plate. In other words, in some embodiments, the size of the heating fluid holes is different at the centre of the heating fluid distribution plate compared to the outer rim of the heating fluid distribution plate.

In other words, preferably only the size of the heating fluid holes, and not the pitch between the heating fluid holes, is changed. Changing the size of the heating fluid holes is more practical than changing the pitch between the holes: pitch changes can result in dead zones if the spacing between the heating holes is too big. Also, for the sake of mechanical stability the heating fluid holes are preferably kept at a certain distance, e.g. at least 1.0 mm or at least 10.0 mm, from the tube holes. Therefore, positioning heating fluid holes with variable pitch is complicated, and heating fluid holes with changing size allow for a much simpler arrangement.

In some embodiments, means for limiting vibrations of the tubes are provided between the heating fluid distribution plate and the bottom end. Preferably, the means for limiting vibrations of the tubes comprise a plurality of rod baffles.

Using rod baffles instead of standard baffles ensures a minimal pressure drop and simultaneously allows for minimal heating fluid flow disruption. A reduced pressure drop allows greater tube density, thus improving stripper capacity for the same stripper size.

In some embodiments, the angle between the longitudinal direction and the heating fluid distribution plate is from 85.0° to 90.0°, or from 87.5 to 90.0°, or from 88.0° to 90.0°, preferably from 89.0° to 90.0°, more preferably from 89.5° to 90.0°, even more preferably 90.0°.

In some embodiments, the angle between the longitudinal direction and the edge wall is from 0.0° to 5.0°, or from 0.0° to 2.5°, or from 0.0° to 2.0°, preferably from 0.0° to 1.0°, more preferably from 0.0° to 0.5°, even more preferably 0.0°.

The term "increasing" as used herein indicates that the parameter to which it refers increases or stays constant and does not decrease in a specified direction and on a specified interval.

The term "strictly increasing" as used herein indicates that the parameter to which it refers increases and does not decrease or stay constant in a specified direction and on a specified interval.

The term "decreasing" as used herein indicates that the parameter to which it refers decreases or stays constant and does not increase in a specified direction and on a specified interval.

The term "strictly decreasing" as used herein indicates that the parameter to which it refers decreases and does not increase or stay constant in a specified direction and on a specified interval.

In some embodiments, the size, e.g. diameter, of the heating fluid holes increases from the outer rim to the centre of the heating fluid distribution plate.

In some embodiments, the size of the heating fluid holes strictly increases from the outer rim to the centre of the heating fluid distribution plate.

In some embodiments, the size of the heating fluid holes decreases from the outer rim to the centre of the heating fluid distribution plate. In some embodiments, the size of the heating fluid holes strictly decreases from the outer rim to the centre of the heating fluid distribution plate.

In some embodiments, the heating fluid distribution plate comprises one or more areas in which the size of the heating fluid holes strictly decreases from the outer rim to the centre of the heating fluid distribution plate, and the heating fluid distribution plate comprises one or more areas in which the size of the heating fluid holes strictly increases from the outer rim to the centre of the heating fluid distribution plate.

Preferably, the holes in the heating fluid distribution plate are drilled.

Preferably, the size of the holes is selected such that during normal operation, the same quantity of heating fluid, e.g. within a margin of error of 10.0%, or 5.0%, or 1.0%, passes through each heating fluid hole.

In some embodiments, the diameter of the heating fluid holes is from at least 1 mm to at most 16 mm, preferably from at least 2 mm to at most 13 mm, more preferably from at least 3 mm to at most 10 mm, even more preferably from at least 5 mm to at most 7 mm.

In some embodiments, the ratio of the diameter of the largest heating fluid holes on the one hand, and the diameter of the smallest heating fluid holes on the other hand is from at least 1.1 to at most 16, preferably from at least 1.4 to at most 3.5.

In some embodiments, the heating fluid holes in the heating fluid distribution plate are evenly spaced at concentric circles around the centre of the heating fluid distribution plate.

In some embodiments, the density of heating fluid holes is constant in the heating fluid distribution plate, and the size of the heating fluid holes changes from the centre of the heating fluid distribution plate towards the outer rim of the heating fluid distribution plate, and the tube holes are arranged in a triangular geometry. A triangular geometry of the tube holes is an arrangement in which the tube holes are arranged at the corners of equilateral triangles. A steam hole is positioned at the centre of each equilateral triangle. In other words, each heating fluid hole is centrally disposed between three adjacent tube holes.

Preferably, six equilateral triangles are arranged to form a hexagonal unit cell.

Preferably, one and only one heating fluid hole is centrally disposed between three adjacent tube holes. Accordingly, the heating fluid holes are also arranged in a triangular geometry. Preferably, the heating fluid holes and the tube holes are arranged in a hexagonal lattice.

Preferably, the geometrical arrangement of tube holes and steam holes is constant over the heating fluid distribution plate, and only the size of the heating fluid holes changes between the centre and rim of the heating fluid distribution plate.

In some embodiments, the density of heating fluid holes is constant in the heating fluid distribution plate, and the size of the heating fluid holes changes from the centre of the heating fluid distribution plate towards the outer rim of the heating fluid distribution plate, and the tube holes are arranged in a square geometry. A simple square geometry of the tube holes is an arrangement in which the tube holes are arranged at the corners of squares. A steam hole is positioned at the centre of each square. In other words, each heating fluid hole is centrally disposed between four adjacent tube holes. Yet differently stated, in a square geometry, four tube holes and a centrally disposed steam holes are arranged to form a square unit cell.

Preferably, one and only one heating fluid hole is centrally disposed between four adjacent tube holes. Accordingly, the heating fluid holes are also arranged in a square geometry. Preferably, the heating fluid holes and the tube holes are arranged in interlocking square lattices.

Preferably, also for the case of a square geometry, the geometrical arrangement of tube holes and steam holes is constant over the heating fluid distribution plate, and only the size of the heating fluid holes changes between the centre and rim of the heating fluid distribution plate.

The terms "triangular geometry" and "square geometry" are equivalent to the terms "triangular lattice" and "square lattice", respectively.

In some embodiments, the stripper comprises more than 3000 tubes, or more than 4000 tubes, or more than 5000 tubes, or more than 6000 tubes, or more than 7000 tubes. In some embodiments, the stripper comprises 3000 to 7000 tubes, or 4000 to 6000 tubes, or 5000 to 7000 tubes, or 5000 to 10000 tubes.

In some embodiments, the shell is cylindrical, and wherein the shell has an outer diameter between 2.0 and 6.0 m, or between 3.0 and 5.0 m.

As mentioned before, the stripper comprises a shell and a plurality of tubes disposed within the shell. In some embodiments, the tubes are vertically disposed within the shell. In some embodiments, the tubes have a length of more than 3.0 m, more than 4.0 m, or more than 5.0 m. In some embodiments, the tubes have a length between 4.0 and 8.0 m, or a length between 5.0 and 7.0 m. Preferably, the tubes have a length between 5.0 and 6.0 m.

The tubes preferably have an outer diameter between 20.0 and 40.0 mm.

In the case of a $CO_2$ stripper, the tubes preferably have an outer diameter between 20.0 and 40.0 mm, or between 25.0 and 35.0 mm.

In the case of a self-stripper, the tubes preferably have an outer diameter between 20.0 and 30.0 mm. In the case of a $CO_2$ stripper, the tubes preferably have an outer diameter between 30.0 and 35.0 mm.

In some embodiments, the tubes have a diameter of up to 32.0 mm, or up to 31.0 mm.

Preferably, the tubes are made of stainless steel.

Further provided herein is a system for the production of urea comprising a carbamate condenser, a urea reactor, and a shell-and-tube stripper as described herein.

The stripper may be, for example, a $CO_2$ stripper or a self-stripper as described above.

In some embodiments, the urea reactor and the carbamate condenser are separate reactor vessels. Alternatively, the urea reactor and the carbamate condenser are realised as an integrated urea reactor and the carbamate condenser. These two embodiments are discussed separately.

When the carbamate condenser and the urea reactor are separate reactor vessels, the carbamate condenser is arranged to partially and exothermically transform ammonia and carbon dioxide into ammonium carbamate, and the carbamate condenser partially converts the thusly formed ammonium carbamate to urea. Thus, a condenser effluent is obtained. The urea reactor is arranged to adiabatically convert at least a part of the ammonium carbamate in the condenser effluent into urea. Thus, a urea/carbamate mixture is obtained. The system is arranged to provide the urea/carbamate mixture to the stripper. The stripper is arranged to convert the urea/carbamate mixture into a urea/carbamate stream concentrated in urea and a gaseous stream comprising carbon dioxide and ammonia.

When the system comprises a combined reactor that serves both as carbamate condenser and urea reactor, the combined reactor is arranged to partially and exothermally transform ammonia and carbon dioxide to ammonium carbamate. In addition, the combined reactor is further arranged to partially convert the ammonium carbamate into urea. Thus, a urea/carbamate mixture is obtained. The system is arranged to provide the urea/carbamate mixture to the stripper and the stripper is arranged to convert the urea/carbamate mixture into a urea/carbamate stream concentrated in urea and a gaseous stream comprising carbon dioxide and ammonia.

Further provided herein is the use of a shell-and tube stripper as described herein for stripping a urea-carbamate mixture.

Further provided is the use of a stripper as described above for improving the stripping efficiency and/or for reducing tube corrosion while stripping urea/carbamate mixtures.

Further provided is a method for stripping a urea/carbamate mixture. Additionally or alternatively, this method can be stated to be a method for reducing corrosion in tubes of strippers for decomposing urea/carbamate mixtures and/or for improving stripping efficiency when stripping urea/carbamate mixtures.

The method comprises the step of providing a shell-and-tube stripper. The stripper is a stripper as described above. Preferably, the stripper is positioned such that the tubes are disposed vertically within the shell. Also, the stripper is preferably positioned such that the top end is on top of the stripper, and the bottom end is at the bottom of the stripper. The urea/carbamate mixture is provided to the inlet for the urea/carbamate mixture.

When a $CO_2$ stripper is used, a stripping gas (i.e. $CO_2$), is provided to the inlet for the stripping gas. When a self-stripper is used, $CO_2$ and $NH_3$ formed during the decomposition of ammonium carbamate serve as the stripping gas. Note that as mentioned above, self-strippers do typically comprise an inlet for passivating air for the purpose of corrosion reduction, but the flow rates of passivating air are insufficient to contribute to the stripping process in a meaningful way.

A heating fluid is provided to the shell-side space by means of a heating fluid inlet. The heating fluid is preferably steam, more preferably saturated steam. The urea/carbamate mixture and the stripping gas are contacted in the tubes. In particular, the urea/carbamate mixture flows as a falling film along the inner walls of the tubes. The stripping gas flows upward in the tube-side space.

The urea/carbamate mixture is heated by means of the heating fluid. Under influence of heat provided by the heating fluid, ammonium carbamate in the urea/carbamate decomposes to form gaseous ammonia and carbon dioxide. As ammonium carbamate in the urea/carbamate mixture decomposes a urea/carbamate stream concentrated in urea is obtained. The urea/carbamate stream concentrated in urea is extracted at the outlet for the urea/carbamate stream concentrated in urea.

A gas mixture comprising the one or more stripped compounds is extracted at the outlet for the gas mixture. When a $CO_2$ stripper is used, this gas mixture comprises the stripping gas as well. The heating fluid is extracted from the shell-side space by means of a heating fluid outlet.

These methods effectively allow better stripping urea/carbamate mixtures while reducing corrosion of strippers.

In some embodiments, the temperature of the tubes is constant along any lateral cross section through the stripper. In some embodiments, the temperature of the tubes is constant along any lateral cross section through the stripper within a margin of error of less than 10° C., less than 5° C., less than 2° C., or less than 1° C. A constant temperature along lateral cross sections through the stripper ensures uniform heat transfer to the tubes. The radially constant temperatures are caused by improved heating fluid distribution and in turn the radially constant temperatures reduce corrosion of the stripper's tubes.

In some embodiments, the pressure in the shell-side space is between 10.0 and 30.0 bar g, preferably between 16.0 and 24.0 bar g.

The mass flow rate of the heating fluid depends on the capacity of the stripper. In some embodiments, the mass flow rate of the heating fluid is between 10.0 and 60.0 kg/s, between 20.0 and 50.0 kg/s, or between 30.0 and 40.0 kg/s.

In some embodiments, the heating fluid comprises steam. Preferably, the heating fluid essentially consists of steam. In other words, the heating fluid preferably comprises at least 99.0 wt % steam, or at least 99.9 wt % steam. The symbol wt % here indicates that the composition of the heating fluid is expressed as a weight percentage, i.e. as the ratio in percent of the mass flow rate of steam comprised in the heating fluid and the mass flow rate of the entire heating fluid.

In some embodiments, the heating fluid has a density between 7.0 and 13.0 kg/m$^3$, or between 8.5 and 12.0 kg/m$^3$.

Further provided herein is the use of a heating fluid distributor for homogenizing the flow of steam near a heating fluid inlet of a shell-and-tube stripper for stripping a urea/carbamate mixture. The heating fluid distributor comprises an edge wall and a laterally disposed heating fluid distribution plate. The edge wall comprises two or more openings and/or a plurality of perforations. The heating fluid distribution plate has an outer rim and a centre, and comprises a plurality of perforations. The plurality of perforations comprises a plurality of tube holes and a plurality of heating fluid holes. The size and/or the density of the heating fluid holes changes from the centre of the heating fluid distribution plate towards the outer rim of the heating fluid distribution plate. Preferably, the heating fluid distributor is a heating fluid distributor as described herein.

EXAMPLES

Example 1

In a first example, reference is made to FIG. 1 which, in panel a), shows a stripper (100) as provided herein. In particular, the stripper (100) is a $CO_2$ stripper. The stripper (100) comprises a shell (160) and a plurality of tubes (150)

which are disposed within the shell (160). Also, the stripper (100) comprises a top end (110) and a bottom end (120). The tubes (150) are disposed between the top end (110) and the bottom end (120). A tube-side space (140) is disposed within the tubes (150). A shell-side space (130) is disposed between the tubes (150) and the shell (160). The shell-side space (130) is separated from the top end (110) and the bottom end (120). The top end (110) and the bottom end (120) are in fluid connection with the tube-side space (140).

The bottom end (120) comprises an outlet (122) for a urea/carbamate stream concentrated in urea and an inlet (121) for a stripping gas.

The top end (110) comprises an inlet (111) for a urea/carbamate mixture and an outlet (112) for a gas mixture that comprises the stripping gas and one or more stripped compounds.

The stripper (100) further comprises a heating fluid inlet (131) and a heating fluid outlet (133). The heating fluid inlet (131) and the heating fluid outlet (133) are in fluid connection with the shell-side space (130). Also, the heating fluid inlet (131) is adjacent to the top end (110) of the stripper (100). The heating fluid outlet (133) is adjacent to the bottom end (120) of the stripper (100).

The tubes (150) have a length of 6.0 m and an outer diameter of 31.0 mm. The stripper has a cylindrical shell with a diameter of 3.1 m.

Rod baffles (134) are positioned at regular intervals in the shell-side space (130). Two specific arrangements of rod baffles are shown in FIG. 1, panel b). Rod baffles as such are known in the art.

The stripper of FIG. 1 comprises a heating fluid distributor comprising a heating fluid distribution plate (175) and an edge wall. The heating fluid distributor ensures that heating fluid flows substantially parallel to the tubes (150) in the part of the stripper between the heating fluid distribution plate (175) and the bottom end (120) of the stripper.

The details of the heating fluid distributor are described in example 3.

Example 2

Figure 2:
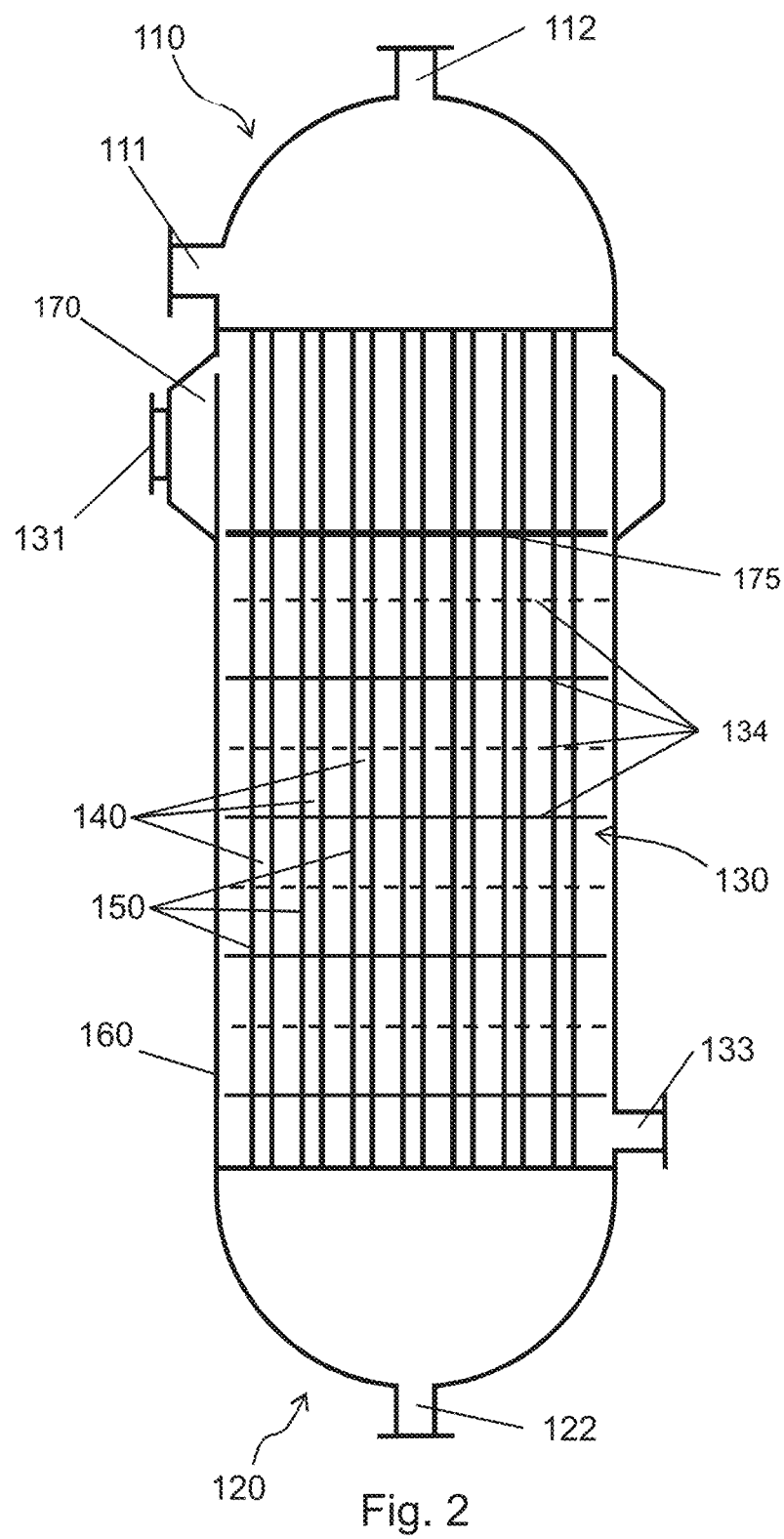
FIG. 2 shows an embodiment of a self-stripper (100).

In a second example, reference is made to FIG. 2 which shows a stripper (100) as provided herein. In particular, the stripper (100) is a self-stripper. The construction of the stripper (100) is similar to that of example 1 with a few differences.

In particular, the self-stripper does not comprise a stripping gas inlet at its bottom end: $NH_3$ and $CO_2$ formed during the decomposition of ammonium carbamate serve as the stripping gas in self-strippers such that there is no need for a stripping gas inlet.

Also, the tubes of the self-stripper are thinner than those of the $CO_2$ stripper of example 1. In particular, the tubes of the self-stripper have an outer diameter of 25 mm.

The stripper of FIG. 2 comprises a heating fluid distributor comprising a heating fluid distribution plate (175) and an edge wall (171) as described in example 3. The heating fluid distributor uniformly distributes heating fluid from the inlet (131) to a belt-shaped space.

Example 3

Figure 3:
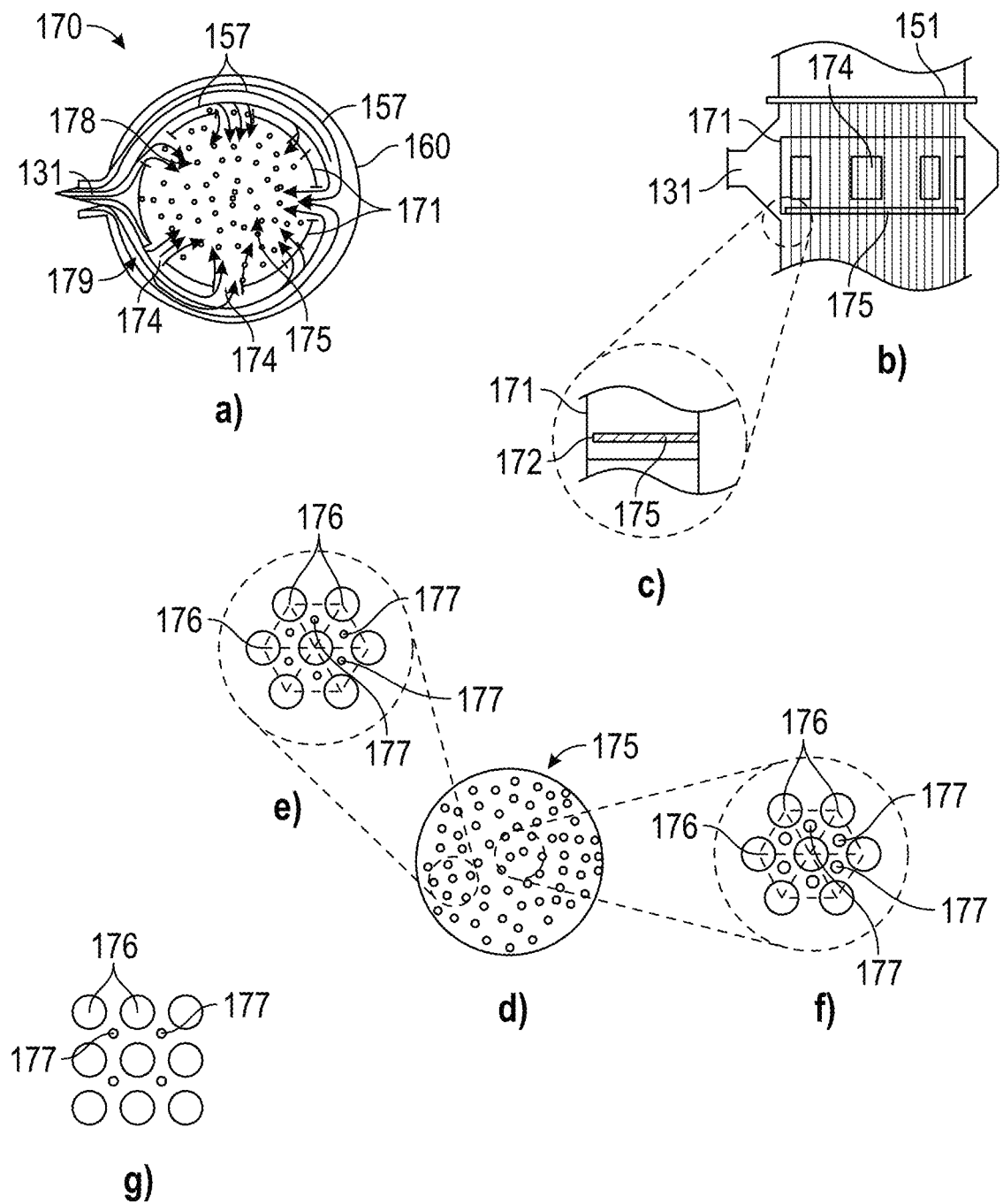
FIG. 3 shows a heating fluid distributor (170) comprising an edge wall (171) and a heating fluid distribution plate (175).

In a third example, reference is made to FIG. 3 which shows several details of an exemplary heating fluid distributor as provided herein. The heating fluid distributor is particularly suitable for providing steam to a shell-side space in a urea stripper.

FIG. 3 comprises 6 panels a) to f).

Panel a) shows a top view on a heating fluid distributor (170) that comprises a heating fluid distribution plate (175) and an edge wall (171). The stripper's shell (160) and the edge wall (171) form a belt-shaped space (179) which accepts heating fluid from a heating fluid inlet (131). The edge wall (171) comprises 7 openings (174) through which heating fluid flows towards an inner heating fluid distribution space (178) above the fluid distribution plate (175), as indicated by stream lines (156). The amount and type of openings (174) depends on the stripper's operating conditions and can vary.

The fluid distribution plate (175) comprises a plurality of steam holes which uniformly distribute heating fluid from the inner heating fluid distribution space (178) to a shell-side space below. The arrangement steam holes are shown in detail in panels d) to g).

Panel b) shows a side view of the heating fluid distributor (170). This panel clearly shows the heating fluid inlet (131), edge wall (171), top tube sheet (151), and heating fluid distribution plate (175).

Panel c) shows that the heating fluid distribution plate (175) does not touch the edge wall (171). Instead, a thermal expansion space is left between the heating fluid distribution plate (175) and the edge wall to take account for thermal expansion. Note that during normal operation, a minor amount of heating fluid may pass through the thermal expansion space (172), but this does not detrimentally influence the heating fluid supply to the shell-side space.

Panel d) shows the heating fluid distribution plate (175).

Panel e) shows a detailed representation of an arrangement of tube holes (176) and heating fluid (177) near the edge of the heating fluid distribution plate. The tube holes (176) are particularly arranged at the corners of equilateral triangles. A heating fluid hole (177) is positioned at the centre of each equilateral triangle. Six equilateral triangles form a hexagonal unit cell.

Panel f) shows a detailed representation of an arrangement of tube holes (176) and heating fluid holes (177) near the centre of the heating fluid distribution plate. This arrangement is similar to the one shown in panel e), the only difference being that the size of the heating fluid holes (176) is different.

Panel g) shows a detailed representation of an alternative arrangement of tube holes (176) and heating fluid holes (177). The tube holes (176) are arranged at the corners of squares. A heating fluid hole (177) is positioned at the centre of each square. Thus heating fluid holes (177) and tube holes (176) are arranged in interlocking simple square lattices. This arrangement of tube holes (176) and heating fluid holes (177) can occur both at the edge and at the centre of the heating fluid distribution plate, the only difference being that the size of the heating fluid holes (176) is different.

Example 4

Figure 4:
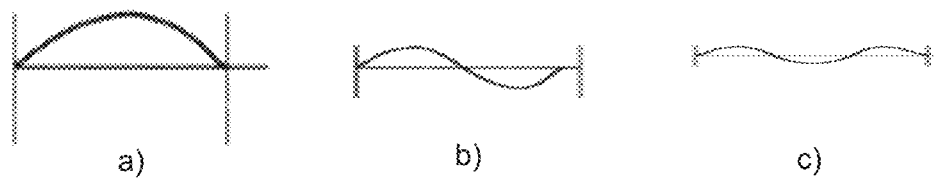
FIG. 4 shows vibration modes of tubes.

In a 4$^{th}$ example, reference is made to FIG. 4 which shows the beneficial effects associated with the use of rod baffles as a means for limiting vibrations of the tubes in the shell-and-tube stripper. In particular, panels a) to c) schematically illustrate the way in which the tubes vibrate for the case of no rod baffles (panel a), 1 rod baffle (panel b), and 2 rod baffles (panel c). Each additional set of baffles introduces an additional node in the tube vibration mode, thereby limiting the amplitude by which the tubes vibrate.

Example 5

Figure 5:
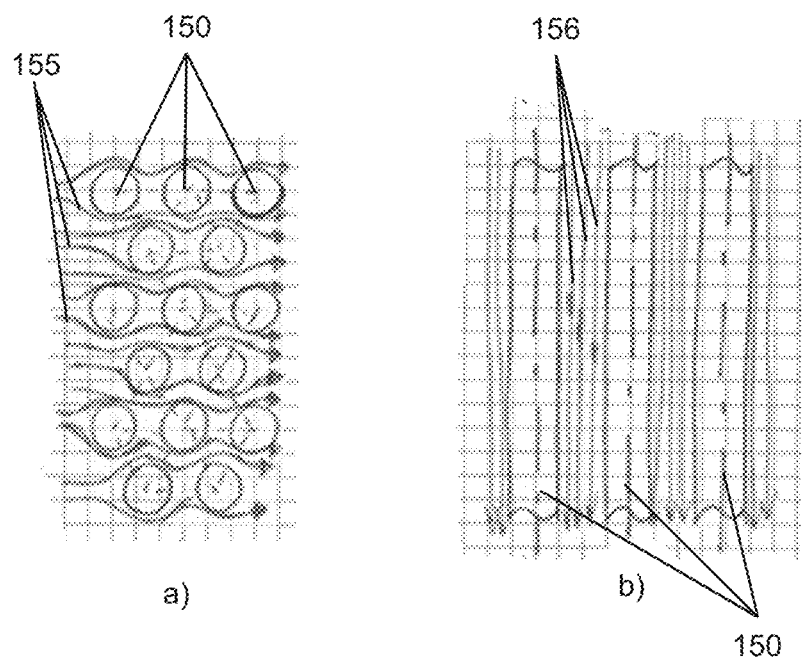
FIG. 5 shows the possible types of flow of a heating fluid between tubes (150).

In a fifth example, reference is made to FIG. 5 which comprises panels a) and b). Panel a) shows heating fluid flow, indicated by stream lines (155) in a lateral direction, i.e. a direction perpendicular to the tubes (150). Such heating fluid flow is minimized by the use of a heating fluid distribution plate (175) as provided herein. Panel b) shows how heating fluid flows parallel to the tubes (150), as indicated by stream lines 156. This is the dominant type of flow induced by the heating fluid distribution plate (175).

Example 6

In a further example, an exemplary method for operating the stripper (100) of example 1 is discussed. In this method, the stripper (100) is positioned vertically, and the top end (110) is positioned at the top of the stripper, and the bottom end (120) is positioned at the bottom of the stripper (100). The stripper comprises a heating fluid distributor comprising a heating fluid distribution plate (175) and an edge wall that is positioned at the heating fluid inlet (131).

The method involves providing a mixture comprising urea and ammonium carbamate to the inlet (111) for the urea/carbamate mixture, and providing $CO_2$, the stripping gas, to the inlet (121) for the stripping gas.

The stripping gas and the urea/carbamate mixture flow in counter-current through the tubes (150). Concurrently, the urea/carbamate mixture is heated and the ammonium carbamate comprised in the urea/carbamate mixture decomposes to form gaseous $NH_3$ and $CO_2$ which are entrained by the stripping gas. Thus, a urea/carbamate stream concentrated in urea is formed in the tubes (150). This stream flows downward to the bottom end (120) where it is extracted by means of the outlet (122) for a urea/carbamate stream concentrated in urea.

Steam is used as a heating fluid, and is provided to the shell-side space (130) by means of a heating fluid inlet (131).

The heating fluid distributor is used to homogenize the flow of steam in the shell-side space. The steam has an operating pressure of about 18 bar (absolute pressure), it has a mass flow rate of 36 kg/sec, and a vapour density of 9 kg/m$^3$.

Condensed steam is extracted from the shell-side space (130) through the heating fluid outlet (133). In traveling from the heating fluid inlet (131) to the heating fluid outlet (133), the steam travels through the shell-side space (130) and heats the tubes (150) and their content, which allows the aforementioned decomposition of ammonium carbamate to form $NH_3$ and $CO_2$.

The provision of the heating fluid distributor ensures homogeneous heating of the tubes (150) and their contents which in turn results in improved stripper efficiency and less corrosion in the tubes.

Example 7

In a further example, an exemplary method for operating the stripper (100) of example 2 is discussed. In particular, its operation is similar to that of the stripper of examples 1 and 6, except that no stripping gas is provided to the bottom end. Instead, $NH_3$ and $CO_2$ formed during the decomposition of ammonium carbamate serve as the stripping gas. Such a stripper is called a self-stripper.

Example 8

Figure 6:
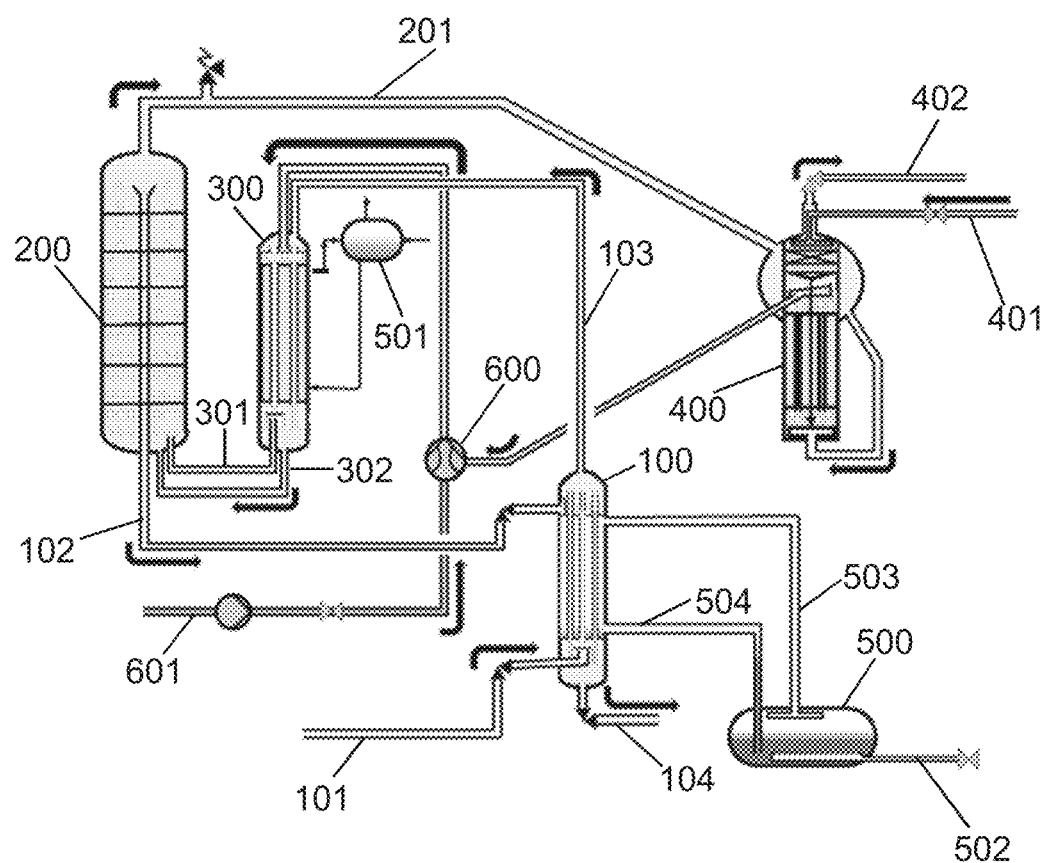
FIG. 6 shows an example of a high-pressure section of a specific type of urea plant in which the presently disclosed technology can be used.

In a further example, reference is made to FIG. 6 which shows selected parts of a urea plant (1000). The urea plant comprises a stripper (100) as described in example 1, a reactor (200) for converting ammonium carbamate into urea, a carbamate condenser (300) for forming ammonium carbamate, and a scrubber (400) for condensing $NH_3$ and $CO_2$ vapours coming from the reactor and the carbamate condenser. The scrubbing liquid is a carbamate solution fed by a tube (401) from a downstream section.

A stripping gas feed (101) is in fluid connection with the inlet (121) for stripping gas of the stripper (100). A tube (104) for a urea/carbamate stream concentrated in urea is in fluid connection with the outlet (122) of the urea/carbamate stream concentrated in urea of the stripper (100).

The stripper (100) comprises a shell-side space see FIG. 1 (130) which comprises a heating fluid inlet and a heating fluid outlet see FIG. 1 (131, 133).

The heating fluid inlet is in fluid connection with a tube for a heating fluid stream (503). The heating fluid outlet is in fluid connection with a tube for a cooled heating fluid stream (504). The tube for a heating fluid stream (503) and the tube for a cooled heating fluid stream (504) are in fluid connection with a heating fluid supply (500), which in turn is in fluid connection with a connection (502) to an external heating fluid supply.

The stripper (100) is further in fluid connection with a tube (102) for a urea/carbamate stream. This tube (102) delivers the urea/carbamate stream from a reactor (200) which transforms ammonium carbamate into urea. The reactor in turn is provided with ammonium carbamate by a carbamate condenser (300) via a tube (302) and with gaseous $NH_3$, $CO_2$, water, and inerts via another tube (301). Heat generated by carbamate formation in the carbamate condenser (300) is extracted by means of steam and a vapour supply (501).

Example 9

In a further example, reference is made to FIGS. 7, 8, 9 and 10 which illustrate some of the challenges which are overcome by way of the systems and methods according to the present invention. In particular, the present systems and methods offer improved stripper life and enhanced stripper efficiency. The present example illustrates these issues for a specific $CO_2$ stripper. However, similar corrosion issues are expected to occur in other types of strippers as well when inhomogeneous heating occurs though the precise corrosion pattern is expected to depend on the specific stripper morphology. One example of a different type of stripper in which similar corrosion issues are expected is a self-stripper.

Figure 7:
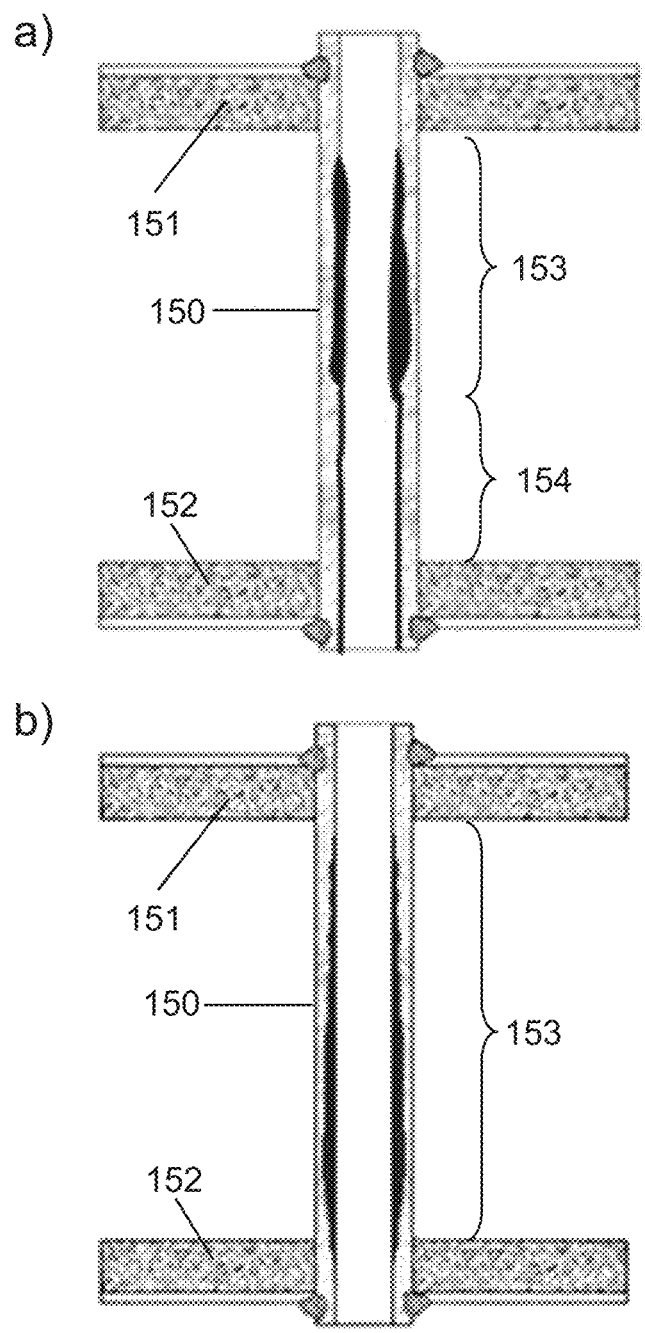
FIG. 7 shows two corrosion patterns which concurrently occur in the tubes of prior art shell-and-tube strippers for stripping urea/carbamate mixtures. In some modes of operation, the corrosion pattern shown in FIG. 7*a* occurs in $CO_2$ strippers and that shown in FIG. 7*b* occurs in self-stripping strippers.

FIG. 7 shows two corrosion patterns that simultaneously occur in sizable state-of-the-art $CO_2$ strippers, with stainless steel tubes, and in which $CO_2$ is used as a stripping gas for stripping a urea/carbamate solution. More specifically, the corrosion pattern was observed in shell-and-tube strippers which have tubes of 6 m high, have a shell diameter of about 3 m, have disk-and-doughnut baffles installed in the shell-side space, and comprise about 5000 tubes (150). The corrosion type also depends on whether the stripper is a $CO_2$ stripper or a self-stripping stripper.

Indeed, the corrosion pattern shown in FIG. 7 a) was found to commonly occur in small-diameter $CO_2$ strippers and that shown in FIG. 7 b) was found to commonly occur in small-diameter self-stripping strippers. In the context of the present invention, both $CO_2$ strippers and self-stripping strippers are specific configurations of shell-and-tube strippers.

These shell-and-tube strippers comprise a top tube sheet (151) which is positioned above and at the top end of the tubes. It separates a shell-side space comprising disk-anddoughnut baffles from the stripper's top end. The top tube sheet (151) also allows a urea/carbamate mixture to flow down as a liquid film along the internal wall of the tubes (150). It also allows a gas mixture comprising $CO_2$ and $NH_3$ to exit the tubes (150).

The shell-and-tube strippers also comprise a bottom tube sheet (152) which is positioned below and at the bottom end of the tubes. It separates the shell-side space from the stripper's bottom end. The bottom tube sheet (152) also allows a urea/carbamate stream concentrated in urea to exit the tubes (150) and in $CO_2$ stripper it allows the $CO_2$ stripping gas to enter the tubes (150).

Figure 8:
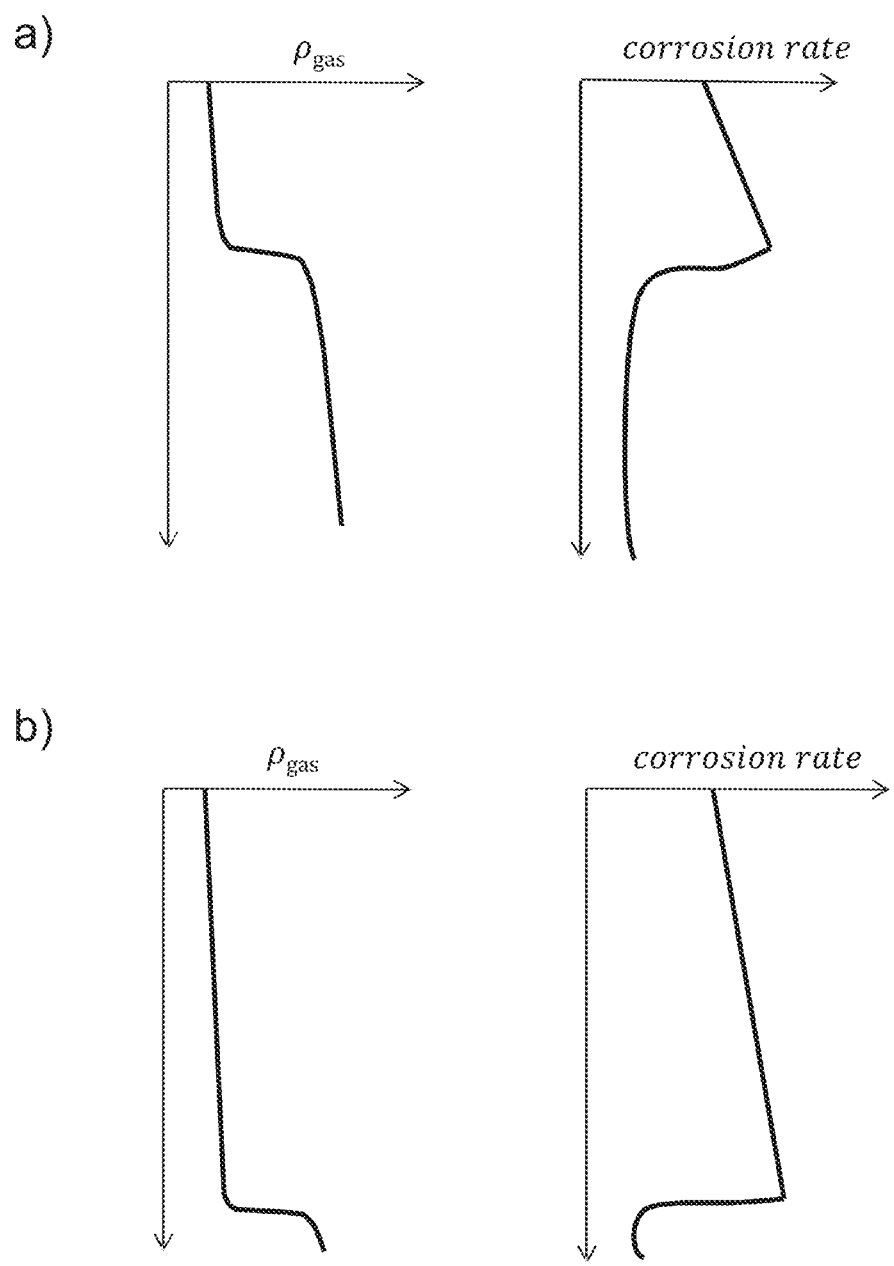
FIG. 8 shows gas densities and corrosion rates which concurrently occur in the tubes of prior art shell-and-tube strippers for stripping urea/carbamate mixtures.

These strippers feature different corrosion patterns in the outer and inner tubes of the stripper. The inner tubes approximately cover the cross-section of the disk baffles, and the outer tubes approximately cover the cross-section of the doughnut baffles. The corrosion pattern in the outer tubes is shown in FIG. 7, panel a). The corrosion pattern in the inner tubes is shown in FIG. 7, panel b). The corrosion rate in the outer tubes is schematically shown in FIG. 8, panel a), right-hand graph. The corrosion rate in the inner tubes is schematically shown in FIG. 8, panel b), right-hand graph.

In the outer tubes, both a corrosion area (153) and a scaling area (154) are present. Conversely, in the inner tubes, only a corrosion area (153) is present. In the corrosion areas, corrosion of the tubes occurs. In the scaling area (154), no corrosion occurs but iron scale is deposited. Although the corrosion area in the outer tubes extends only along part of the length of the tubes, the corrosion is much more severe in the corrosion area (153) of the outer tubes. The useful life of strippers is limited by the rate of corrosion of the tubes. Therefore, if the rate of corrosion occurring in the outer tubes (150) could be reduced, the extent of corrosion after a certain period in operation would be reduced, and consequently the useful life of the strippers could be increased.

Without restricting the present invention to any particular mode of operation, it is believed that the occurrence of the inhomogeneous corrosion in prior art $CO_2$ strippers for stripping ammonium carbamate from urea/carbamate streams can be explained as follows. During normal operation of prior art strippers, a urea/carbamate mixture flows down the internal wall of the tubes (150) as a falling film pattern, and it is heated by means of steam provided to the shell-side space. Under influence of the heat, the ammonium carbamate in the urea/carbamate mixture decomposes to form gaseous $NH_3$ and $CO_2$, which flow upward along with the stripping gas. Thus ammonium carbamate is gradually decomposed.

In arriving at the present invention, it was realised that the presence of iron scales in the lower part of the outer tubes, i.e. the scaling part (154), indicates that in the scaling part, the liquid phase consists mainly of urea, residual carbamate, free $NH_3$ and water. In other words, a large portion of the ammonium carbamate has decomposed, thereby leaving a liquid phase essentially consisting of urea, residual carbamate, free $NH_3$ and water that flows down the tube walls at the scaling part (154): Iron (Fe) is significantly less soluble in urea than in ammonium carbamate. Conversely, the centre tubes do not have a scaling part, which indicates that ammonium carbamate has not entirely been decomposed.

It was further realised that the rate at which the ammonium carbamate is decomposed increases with an increasing amount of heat which is provided to the tubes (150). Accordingly, the observation that ammonium carbamate decomposes closer to the top end of the stripper in the outer tubes indicates more intense heating in the outer tubes compared to the inner tubes. Because the heat is provided by means of steam flowing on the shell-side space of the stripper, the amount of heat is determined by the flow of steam. Therefore, the provision of more heat to the outer tubes compared to the inner tubes is related to the flow of steam in the shell-side space of the stripper. The inventors thus discovered that inhomogeneous flow of steam in the shell-side space of the stripper is the cause for the observed increased corrosion rate in the outer tubes compared to the inner tubes.

It was additionally discovered that the inhomogeneous heating of the tubes results in inefficient operation of strippers related to inhomogeneous $CO_2$ stripping gas distribution over the tubes. In particular, it was found that under typical operating conditions of prior art shell-and-tube strippers featuring a steam inlet and disk-and-doughnut baffles in the shell-side space, the gas flow rate through the less-heated inner tubes is significantly higher than the gas flow rate through the more heated outer tubes. Inhomogeneous stripping gas flow leads to process inefficiencies such as the inhomogeneous stripping of the carbamate in the tubes and consequently an ineffective decomposition of ammonium carbamate in the stripper.

Figure 10:
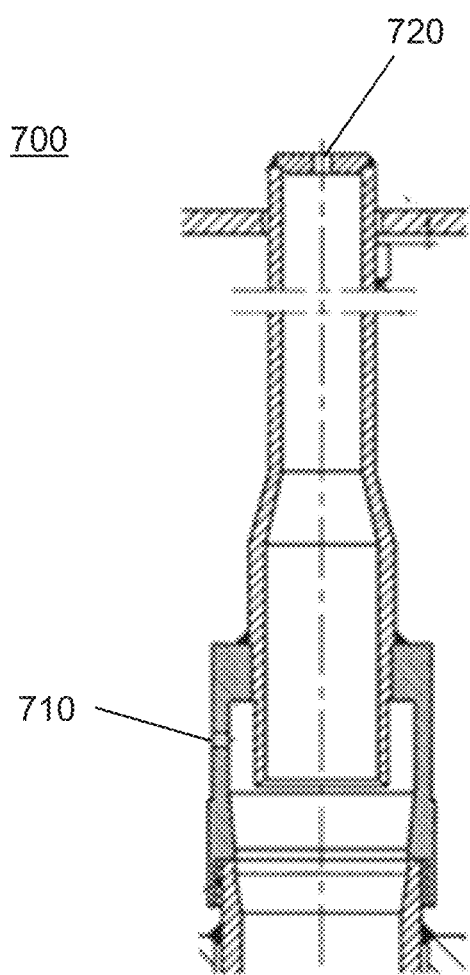
FIG. 10 shows an example of a ferrule (700).

Liquid dividers (so called ferrules, an example of which is shown in FIG. 10), are installed in the stripper front head and coupled with tubes in the top tube sheet in order to assure an even distribution of the urea/carbamate mixture though each tube via holes (710) in the bottom part of the ferrule. Also, one or more holes (720) in the liquid divider top part are installed to release the gas flow to the stripper top end. The stripping gas flow is determined by a combination of hydrodynamic and hydrostatic effects. The hydrodynamic effects correspond to the pressure drop across the one or more holes (720) in the top liquid dividers (so called ferrules), and can be written as $\Delta p = 0.5 \rho v^2$, with $\Delta p$ pressure drop, $\rho$ fluid density, and $v$ fluid velocity.

For typical operating conditions, the hydrodynamic pressure drop across the tubes is about 250 Pa. The hydrostatic effect corresponds to the pressure effect due to the gas density along the height of the tubes, and, for a given pressure, can be written as $\Delta p = \Delta \rho g h$. The hydrostatic pressure drop in the stripper that was described above is estimated to be about 5500 Pa. Accordingly, the hydrostatic effect dominates, and it is therefore mostly responsible for the stripping gas flow distribution across the tubes. Therefore, any possible imbalance in stripping gas flow between the tubes caused by differences in hydrostatic pressure drop across the tubes cannot be compensated by changing the hydrodynamic pressure drop across the hole on top of the ferrules. The pressure drop across the hole might be changed by changing the size of the hole in the ferrule. By reducing the hole size the pressure drop would increase and vice versa.

It was discovered that in more heated tubes, carbamate decomposition and the accompanying release of $CO_2$ and $NH_3$ occurs in the top parts of the tubes, i.e. near the top end, e.g. in the upper 50% of the tubes. Therefore, the partial pressure of $NH_3$ at the top of the tubes is high, whereas the partial pressure of $NH_3$ in the bottom part of the tubes is low. The stripping gas is $CO_2$, and under the same conditions, $NH_3$ has a lower density than $CO_2$. Because the gas flows upward, the $NH_3$ concentration is highest in the top part of the tubes. Therefore, the top part of the tubes has a lower specific density than the bottom part of the tubes. This is illustrated in FIG. 8, panel (a). This figure shows that the tubes comprise three regions: a lower region featuring a higher gas density and lower corrosion rate, a transition region in which the gas density and the corrosion rate suddenly change, and an upper region which has a higher corrosion rate and a lower gas density. In particular, going up the tubes, the first region the gas encounters is the lower region. In the lower region, the gas density gradually decreases as the gas is heated while it travels up the tubes. In the transition region the gas density suddenly decreases due to the decomposition of ammonium carbamate and the resulting release of ammonia gas. In the upper region, the gas density gradually decreases as the gas is further heated, and the corrosion rate is high because the tube walls are in contact with an intensely heated urea/carbamate solution. Indeed, the corroded thickness of the tube increases moving downwards within the upper region, as the solution gets warmer while moving downwards.

Also, the inventors discovered that in less heated tubes, carbamate decomposition occurs from the top of the tube until close to the bottom of the tubes, such that the entirety of the less heated tubes has a lower specific density compared to the more heated tubes, which in turn causes the hydrostatic pressure in the less heated tubes to be lower than the hydrostatic pressure in the more heated tubes.

Figure 9:
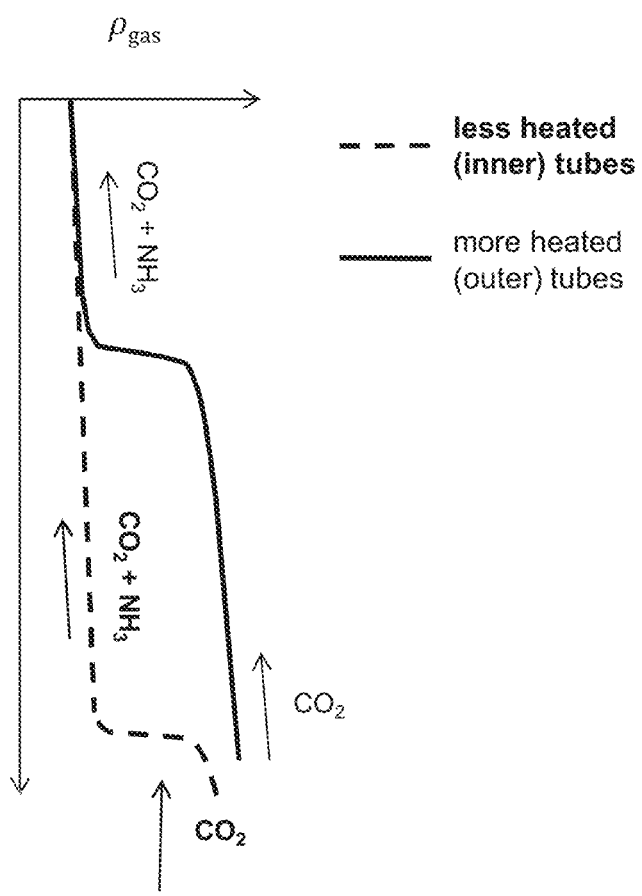
FIG. 9 is a schematic representation of gas density as a function of position in less-heated tubes and more heated tubes.

The gas density profile of the more heated outer tubes is shown in FIG. 8, panel a), left-hand graph. The gas density profile of the less-heated inner tubes is shown in FIG. 8, panel (b), left-hand graph. The gas density profile in the less heated tubes and the more heated tubes is also compared in FIG. 9. FIG. 9 clearly shows that in the less heated tubes, carbamate decomposes near the bottom of the stripper compared to the more heated tubes. This results in a different density profile, which in turn causes a hydrostatic pressure difference. The lower hydrostatic pressure in the inner tubes causes the flow rate of the stripping gas in the less heated tubes to be higher than in the more heated tubes, which results in lower stripping efficiency.

This is slightly counteracted when $CO_2$ stripping gas with a lower temperature than the tubes is used, because the cooler $CO_2$ gas lowers the density of the gas phase in the tube, thereby increasing the hydrostatic pressure and counteracting the effect of the increased heating. However, this effect is not sufficiently pronounced to eliminate the stripping inefficiencies associated with inhomogeneous heating.

Indeed, simulations (results not included) showed that even a small difference in the density profile results in a significant effect on the flow distribution. In particular, the area-weighted average fluid flow velocity in the less-heated inner tubes was estimated to be ca. 5 times higher than the area-weighted averaged fluid flow velocity in the more heated outer tubes. This large discrepancy in fluid flow velocity results in significant stripping inefficiencies in prior art strippers.

In conclusion, inhomogeneous heating in sizable prior art $CO_2$ strippers results in corrosion issues and inefficient stripping. This problem can be solved by providing a heating fluid distributor as described herein; thus allowing homogeneous heating such that all tubes of the stripper can be heated moderately and uniformly, which results in a low rate of corrosion throughout the stripper. In addition, the homogeneous heating results in a homogeneous gas density profile, which in turn results in a uniform stripping gas flow rate and improved stripping efficiency.

The invention claimed is:

1. A shell-and-tube stripper for stripping a urea/carbamate mixture, the stripper comprising a top end in fluid connection with a bottom end through a plurality of tubes disposed within a shell;

the top end comprising an inlet for a urea/carbamate mixture and an outlet for a gas mixture comprising a stripping gas and one or more stripped compounds;

the bottom end comprising an outlet for a urea/carbamate stream concentrated in urea;

the shell-and-tube stripper further comprising a heating fluid inlet and a heating fluid outlet in fluid connection with a shell-side space disposed between the plurality of tubes and the shell;

the shell-and-tube stripper having a longitudinal direction and lateral cross sections, the longitudinal direction being parallel to the tubes and the lateral cross sections being perpendicular to the longitudinal direction;

wherein the shell-and-tube stripper comprises a heating fluid distributor adjacent to the heating fluid inlet for homogenizing a flow of heating fluid in the stripper, the heating fluid distributor comprising an edge wall and a heating fluid distribution plate which is disposed parallel to the lateral cross sections;

the edge wall comprising two or more openings and/or a plurality of perforations, and the edge wall defining a belt-shaped space between the shell and the edge wall;

the heating fluid inlet being arranged for providing heating fluid to the belt-shaped space;

the belt-shaped space being arranged for providing heating fluid to an inner heating fluid distribution space;

the heating fluid distribution plate being arranged for providing heating fluid from the inner heating fluid distribution space to the shell-side space between the heating fluid distributor and the bottom end;

the heating fluid distribution plate comprising a plurality of perforations, the plurality of perforations comprising a plurality of tube holes and a plurality of heating fluid holes, wherein a size and/or a density of the heating fluid holes changes in a radial direction of the heating fluid distribution plate.

2. The shell-and-tube stripper according to claim 1 wherein the size of the heating fluid holes changes from a center of the heating fluid distribution plate towards an outer rim of the heating fluid distribution plate.

3. The shell-and-tube stripper according to claim 2 wherein the size of the heating fluid holes increases from the outer rim to the center of the heating fluid distribution plate; or wherein the size of the heating fluid holes decreases from the outer rim to the center of the heating fluid distribution plate.

4. The shell-and-tube stripper according to claim 2 wherein the heating fluid distribution plate comprises one or more areas in which the size of the heating fluid holes strictly decreases from the outer rim to the center of the heating fluid distribution plate, and wherein the heating fluid distribution plate comprises one or more areas in which the size of the heating fluid holes strictly increases from the outer rim to the center of the heating fluid distribution plate.

5. The shell-and-tube stripper according to claim 1 wherein means for limiting vibrations of the tubes are provided between the heating fluid distribution plate and the bottom end.

6. The shell-and-tube stripper according to claim 5, wherein the means for limiting vibrations of the tubes comprise a plurality of rod baffles.

7. The shell-and-tube stripper according to claim 1 wherein an angle between the longitudinal direction and the heating fluid distribution plate is from 85.0° to 90.0°; and/or wherein an angle between the longitudinal direction and the edge wall is from 0.0° to 5.0°.

8. The shell-and-tube stripper according to claim 7 wherein the angle between the longitudinal direction and the heating fluid distribution plate is 90.0°; and/or
wherein the angle between the longitudinal direction and the edge wall is 0.0°.

9. The shell-and-tube stripper according to claim 1 wherein a diameter of each of the heating fluid holes is from at least 1 mm to at most 16 mm; and/or wherein a ratio of the diameter of a largest of the heating fluid holes to the diameter of a smallest of the heating fluid holes is from at least 1.1 to at most 16.

10. The shell-and-tube stripper according to claim 9 wherein the diameter of each of the heating fluid holes is from at least 5 mm to at most 7 mm.

11. The shell-and-tube stripper according to claim 1 wherein the heating fluid holes in the heating fluid distribution plate are evenly spaced at concentric circles around a center of the heating fluid distribution plate.

12. The shell-and-tube stripper according to claim 1 wherein the density of heating fluid holes is constant in the heating fluid distribution plate, wherein the size of the heating fluid holes changes from a center of the heating fluid distribution plate towards an outer rim of the heating fluid distribution plate, wherein the tube holes are arranged in a triangular geometry, and wherein each heating fluid hole is centrally disposed between three adjacent tube holes.

13. The shell-and-tube stripper according to claim 1 wherein the density of heating fluid holes is constant in the heating fluid distribution plate, wherein the size of the heating fluid holes changes from a center of the heating fluid distribution plate towards an outer rim of the heating fluid distribution plate, wherein the tube holes are arranged in a square geometry, and wherein each heating fluid hole is centrally disposed between four adjacent tube holes.

14. The shell-and-tube stripper according to claim 1 wherein the stripper comprises more than 3000 tubes.

15. The shell-and-tube stripper according to claim 14, wherein the stripper comprises 5000 to 10000 tubes.

16. The shell-and-tube stripper according to claim 1, wherein the bottom end comprises an inlet for the stripping gas.

17. A system for production of urea comprising a carbamate condenser, a urea reactor, and a shell-and-tube stripper according to claim 1.

18. A heating fluid distributor for homogenizing a flow of steam adjacent to a heating fluid inlet of a shell-and-tube stripper for stripping a urea/carbamate mixture, the heating fluid distributor comprising an edge wall and a heating fluid distribution plate which is disposed parallel to lateral cross sections of the shell-and-tube stripper;

the edge wall comprising two or more openings and/or a plurality of perforations, the heating fluid distribution plate having an outer rim and a center, the heating fluid distribution plate comprising a plurality of perforations, the plurality of perforations comprising a plurality of tube holes and a plurality of heating fluid holes, wherein a size and/or a density of the heating fluid holes changes from the center of the heating fluid distribution plate towards the outer rim of the heating fluid distribution plate.

19. A method for stripping a urea/carbamate mixture, the method comprising steps of:

providing a shell-and-tube stripper according to claim 1;

providing the urea/carbamate mixture to the inlet for the urea/carbamate mixture;

providing a heating fluid to the shell-side space by means of the heating fluid inlet, wherein the heating fluid is saturated steam;

contacting the urea/carbamate mixture and the stripping gas in a tube-side space disposed within the tubes, and heating the urea/carbamate mixture by means of the heating fluid, thereby obtaining a urea/carbamate stream concentrated in urea;

extracting the urea/carbamate stream concentrated in urea at the outlet for the urea/carbamate stream concentrated in urea;

extracting a gas mixture comprising one or more stripped compounds at the outlet for the gas mixture, the one or more stripped compounds comprising $NH_3$, $CO_2$, and water;

extracting the heating fluid at the heating fluid outlet.

20. The method according to claim 19, further comprising a step of providing a stripping gas to an inlet for the stripping gas at the bottom end.

* * * * *